(12) United States Patent  
Miqui

(10) Patent No.: US 8,801,430 B2  
(45) Date of Patent: Aug. 12, 2014

(54) BRACKET IMPROVEMENT WITH INTERCHANGEABLE LOCKS

(76) Inventor: Carlos Edwardo Miqui, Säo Paulo (BR)

( * ) Notice: Subject to any disclaimer, the term of this patent is extended or adjusted under 35 U.S.C. 154(b) by 0 days.

(21) Appl. No.: 11/382,846

(22) Filed: May 11, 2006

(65) Prior Publication Data

US 2006/0269891 A1    Nov. 30, 2006

(30) Foreign Application Priority Data

May 30, 2005    (BR) ..................... 0502124

(51) Int. Cl.  
*A61C 7/34* (2006.01)

(52) U.S. Cl.  
USPC .................. 433/13; 433/10; 433/16

(58) Field of Classification Search  
USPC .............. 433/8–10, 13–17, 11–12  
See application file for complete search history.

(56) References Cited

U.S. PATENT DOCUMENTS

| | | | | | |
|---|---|---|---|---|---|
| 2,908,974 | A | * | 10/1959 | Stifter | 433/16 |
| 3,128,552 | A | * | 4/1964 | Broussard | 433/13 |
| 4,180,912 | A | * | 1/1980 | Kesling | 327/437 |
| 4,487,581 | A | * | 12/1984 | Adler | 433/16 |
| 4,597,739 | A | * | 7/1986 | Rosenberg | 433/16 |
| 4,676,746 | A | * | 6/1987 | Klapper | 433/16 |
| 5,302,121 | A | * | 4/1994 | Gagin | 433/10 |
| 5,738,513 | A | * | 4/1998 | Hermann | 433/13 |
| 6,695,612 | B2 | * | 2/2004 | Abels et al. | 433/10 |
| 7,033,170 | B2 | * | 4/2006 | Cordato | 433/10 |
| 2004/0029066 | A1 | * | 2/2004 | Goldschmied | 433/14 |

* cited by examiner

*Primary Examiner* — Cris L Rodriguez  
*Assistant Examiner* — Edward Moran  
(74) *Attorney, Agent, or Firm* — McKee, Voorhees & Sease

(57) ABSTRACT

A bracket is used in orthodontic treatment with a base fixed to the tooth with a constructive arrangement able to receive locks capable of providing infinite mechanical needs of orthodontic treatment, providing the efficient positioning of the traction wires in order to increase the versatility of the apparatus itself, resulting in an optimized and less painful treatment than the conventional brackets.

1 Claim, 7 Drawing Sheets

BRACKET IMPROVEMENT WITH INTERCHANGEABLE LOCKS

BACKGROUND OF THE INVENTION

The said brackets are individual pieces that can be used by specific sets of teeth that have autonomy on the crown and in similar positions, being glued to the teeth using specific resins.

Each bracket has a certain torque value that is transmitted to the tooth in accordance with the positioning of the base on the vestibule surface of the tooth in question.

As has already commented, each tooth has a specific bracket with predetermined torques and angles, it being possible in some case to interchange the brackets between the teeth to most conveniently adjust the torques and angles to obtain certain movements. However, any change has consequences. This is because the teeth have distinct anatomies, in other words, whenever brackets are changed between groups of teeth, most probably their position changes and as a result the intended expression may not be obtained.

Based on the positioning of the bracket arches are used that help to express the established measures, in other words, the traditional manner of movement the brackets and teeth is through the arches, which with the actuation hinges move the teeth to the desired position. The function of the arch is upon establishing contact with the groove, in the returning movement to the original format to bring the tooth to a position pre-established by the arch.

The wires currently used are of the so-called third generation, which consists of wires with a memory that can be used for long periods—up to one year without the need to change the arch.

The tying of the arch to the traditional bracket is made with steel or elastic ties.

At the beginning of traditional treatment arches with less force are used, since the need to movement them in this stage is greater.

The traditional manner of using less force is to use lighter wires, in which the force exerted by the wire is determined by three variables around the same arch used, where the bracket is completely passive, with the variables being as follows:

Length of wire—the longer the wire, the lesser the force. Length is determined through individualized configurations in various formats.

Diameter of wire—the greater the diameter the greater the force. At the beginning of the treatment lighter wires—i.e., with smaller diameters—are used rather than those used at the end.

Wire material—according to the material used there are different hardness levels. For comparison, the stainless steel, the most used wire in this segment, has a hardness index equal to 1, while TMA has an index of 0.42 and the memory wire has an index between 0.08 and 0.16. Therefore, using an arch with the same diameter, though of different materials produces different forces.

In terms of mechanics there are also problems with the conventional system, since movement is obtained through the use of brackets systems and wires acting jointly, however there is a limitation on the force that can be used. In a case example, the practitioner has to choose the groove taking into account the sizes available in the market, with the majority opting for one of the sizes already available in the market between 0.018" and 0.022". Afterwards the orthodontist has to opt for the proper prescription to the patient, taking into account the level of force and movement desired already allowing for undesirable movements during the treatment.

Normally practitioners tend to keep only one prescription in stock in order to reduce fixed costs (money invested without return), since it means having stocks that might never be used. To begin the treatment, since the deformations in the dental arch are at their highest level, usually the lightest arches are used, in other words more flexible material with a smaller diameter. However, in mechanical terms and in relation to adverse effects, it has to be taken into account that to move a tooth if, for example, a 0.022"×0.025" rectangular section arch is being used (currently the largest diameter in orthodontics) in a 0.022"×0.030 groove, the gap between the wire and the groove will be substantially zero. Whereas if a 0.016"×0.022" wire is used instead (intermediate wire) there will be a gap of 27.4° according to the specific table. Therefore, in practical and mechanical terms to move a tooth backwards (normal mechanical retraction in cases of extraction) a 0.017"×0.025" or 0.019"×0.025" section arch is usually used in a 0.022" high groove, the gap according to the specific table is between 17.7° and 10.5°, in other words the tooth can begin in a position in which it has a 15° torque and finish with 2.7° to 1.5°, which is sufficient for finalization. As a result of this, at the end of the above-mentioned movement, the tooth has to be brought to the 15° required to finish, through a torque movement obtained by folding the wire. Though the most adequate or desired movement would be that of the body without any unwanted inclinations.

In the current state of art, brackets, being limited by the manufacturing processes currently available, have a constructive arrangement forming a single body and, even with the creation of new manufacturing technologies, hardly anything has been changed, the opening of the groove continuing to be made by the backside surface.

Such construction, although currently used in large scale, presents as main inconveniences the lack of measuring flexibility, which in actual fact means that in case the practitioner needs to change a torque or an inclination, he will have to bend the wire or change the bracket. Another inconvenience relate to the need of the tie to adjust the wire to the bottom of the groove. Since the groove is open, the only way to fix the wire to its bottom is through said ties, which can be made of steel or a stretching material. Finally, the only way to increase or decrease the force the arch conveys to the tooth is changing the wire diameter.

Upon analyzing all the aforementioned inconveniences, the inventor, a practitioner in the orthodontic area, created a versatile bracket able to attend the requirements and happenstances which may occur during the treatment, i.e., a bracket adjustable to infinite possibilities of occurrences.

The bracket object of this invention encompass in general lines a base fixed to the tooth, of constructive arrangement suitable to perfectly adhere to the vestibular portion of said tooth, with possibility to receive several lock types that once overlapped to the bases allow to diversify the "groove" according to the most pressing treatment requirements without the need to change the entire bracket or larger adjustments of the wires that form the traction arch. Once the lock is overlapping to the base, a set of anatomical and more comfortable external lines is obtained. With the claimed bracket, there is greater flexibility for using the same arch, possible to gauge the force intensity conveyed by the lock change.

Therefore, from this invention a series of extraordinary advantages arises, of practical and functional nature, particularly oriented to achieve treatment optimization and greater comfort to the patient.

More specifically, for instance, at the treatment initial phase, it is possible to have a bracket with larger "groove", which together with a low diameter arch impart the set larger flexibility and less force, which immediately increases the patient's comfort.

To better illustrate, in the case example of a 0.030" height "groove" associated to a 0.014" diameter wire formed by more elastic alloys is extremely comfortable to the patient, while coupled with the low friction, it will allow more agile movement within the biological limits. For such the relative hardness of each material type should also be analyzed according to specific tables.

Still illustrating the invention in a practical manner, after the first phase or initial phase, a lock can be used that allow an intermediate height "groove" that together with wires with diameter larger than the initially used wires, allow greater control, ideal for this stage of the treatment. For instance, a set with 0.022" height groove, arcs with 0.014"×0.025" or 0.016"×0.025".

Finally, each tooth can be individualized in a customized manner specific to the patient's needs, i.e., if a distinctive torque is required for a certain tooth, the lock can simply be changed and the wire passed without the need for plication. More particularly, it is possible to have variations between the final phases of the treatment wherein the tooth can begin with a larger torque bracket, e.g. 22° for retraction mechanics and finish with a smaller torque, e.g. 15° or 7° without the need to entirely change the bracket, which could damage the tooth enameling, it being enough to just change the lock. Another possibility is going to the finishing stage, coupling a lower height "groove" with a smaller diameter arch with hardly any gap, but greater rigidity, without the need to actually increase the force level and consequent patient discomfort, such as, for instance, a 0.016" groove with a 0.016"×0.025" arch, i.e., instead of using a larger diameter stainless steel arch, such as, for instance, a 0.021"×0.025", with relative hardness of 2176 according to specific table, it is possible to use a 0.016"×0.022" arch with relative hardness of 1130, almost half the force, however with equivalent gap and control.

In fact, it is possible to go through all the treatment stages using practically only one memory arch, which are extremely comfortable due to the low force applied and even arrive to the finishing stage with possibility of using the same arch, simply changing the locks. Even during the intermediate mechanics it is possible to obtain extraordinary variables from the current mechanics without the unwanted side effects.

Still in the advantage field, we highlight: quickness, versatility, customization, precision and optimization.

BRIEF SUMMARY OF THE INVENTION

Bracket improvement with interchangeable lock encompass a bracket (1) formed by a base (2) of fixed construction arrangement to which the vestibular portion (3) of the tooth is adhered, in view of having angling (4) therefor, such base (2) with orthogonal projection (5) which can receive locks (6) overlapped with several angling and "groove" dimensions (7) shaped on its side wall (8) that, once overlapped to the base (2) creates an ideal passageway for conduction of wires (F) of different gauges, it being enough to change said locks (6) to fit the "grooves" (7) according to pressing treatment need, the same base (2) remaining throughout the treatment.

FIGURE

1—Tolerances for face-to-face distances, center to center: 3 mm
2—Connection alignment: 1.5 mm
3—Maximum flange spacing from the position indicated in the project: 1.5 mm
4—Misalignment of holes per flange rotation in relation to the correct position: 1.5 measured as indicated in Figure.
5—Flange shifts or variances from the position indicated in the project: 1.5 mm
6—In bent tubes the difference between the maximum and minimum diameter (flattening) cannot exceed 8% of outer diameter with inner pressure and 3% with outer pressure.
7—Inclination angle of the flange in relation to the line

BRIEF DESCRIPTION OF DRAWINGS

In following, the invention shall be explained with regard to the attached drawings, wherein are represented.

DETAILED DESCRIPTION OF THE INVENTION

Figure 1:
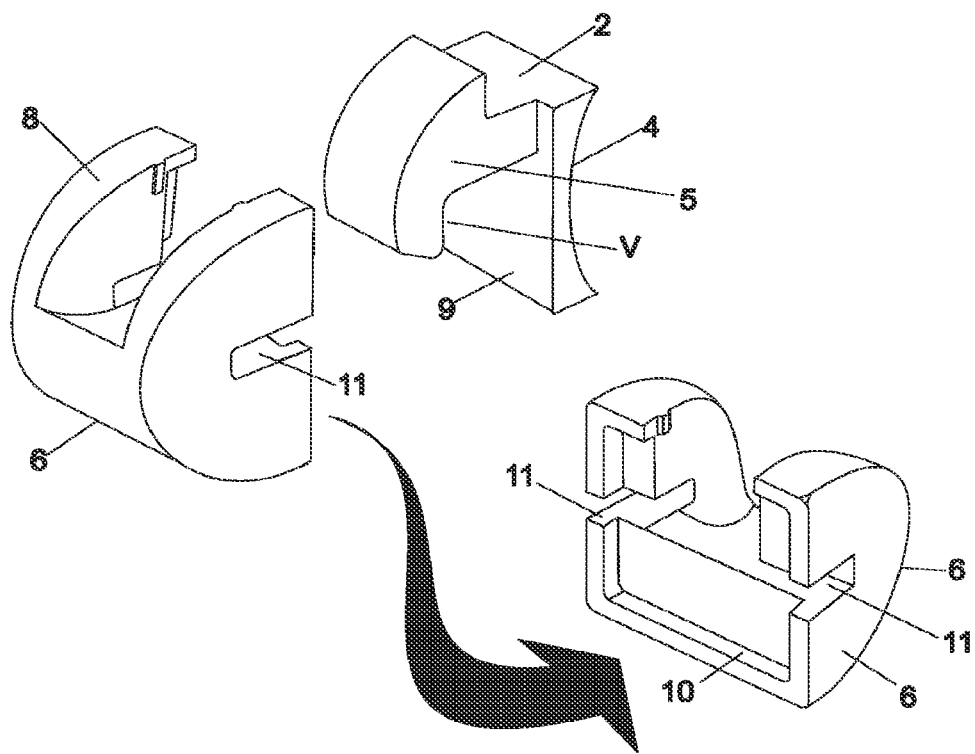
FIG. 1: Exploded perspective view of bracket improvement with interchangeable lock, shown in the neutral position.
Figure 2:
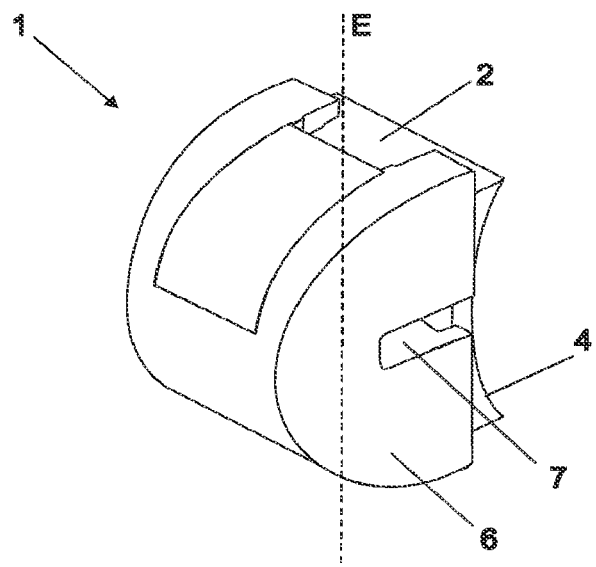
FIG. 2: Perspective view of bracket improvement with interchangeable lock, shown in the neutral position.
Figure 3:
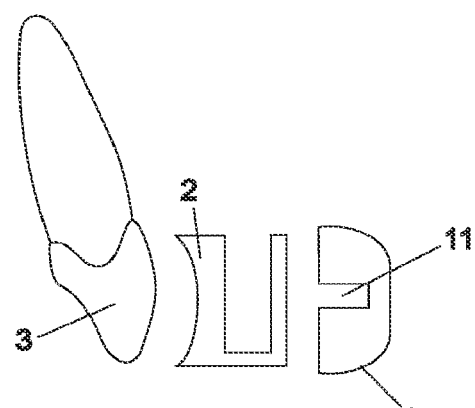
FIG. 3: Illustration of a basic application wherein on a schematic exploded side view the base and the lock to obtain a neutral torque is shown.
Figure 4:
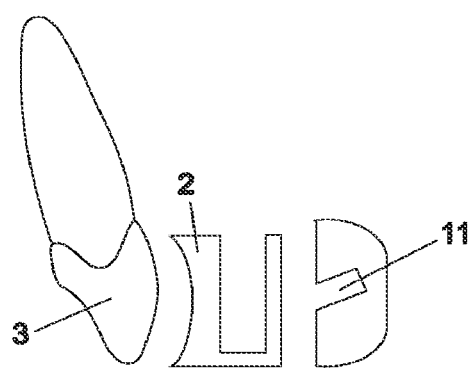
FIG. 4: Illustration of a basic application wherein on a schematic exploded side view the base and the lock to obtain a positive torque is shown.
Figure 5:
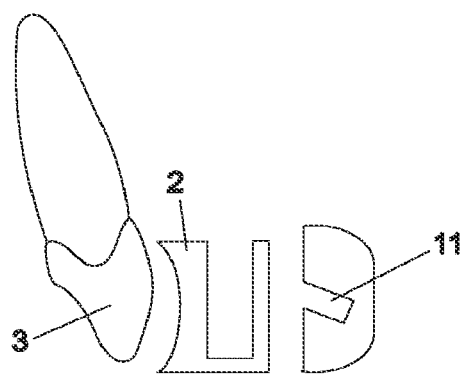
FIG. 5: Illustration of a basic application wherein on a schematic exploded side view the base and the lock to obtain a negative torque is shown.
Figure 6:
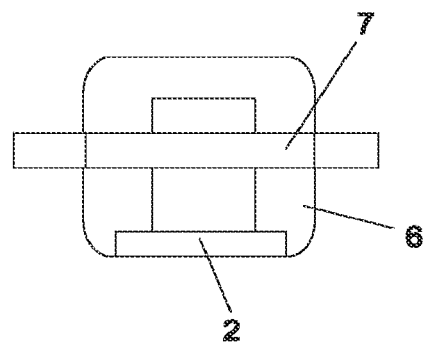
FIG. 6: Illustration of a basic application wherein on a schematic side view the base and the lock to obtain neutral inclination is shown.
Figure 7:
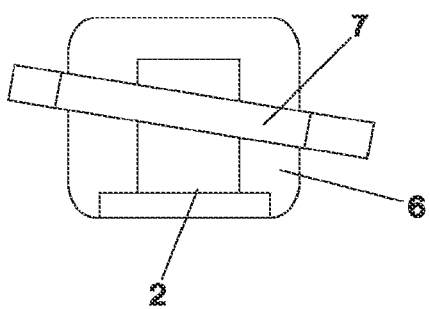
FIG. 7: Illustration of a basic application wherein on a schematic side view the base and the lock to obtain positive inclination is shown.
Figure 8:
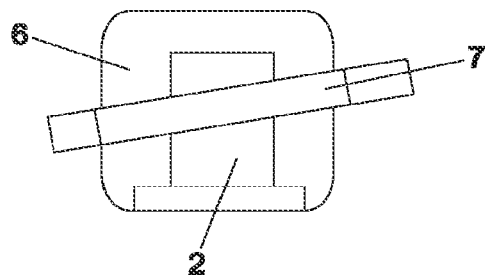
FIG. 8: Illustration of a basic application wherein on a schematic side view the base and the lock to obtain negative inclination is shown.
Figures 9A, 9B, 9C:
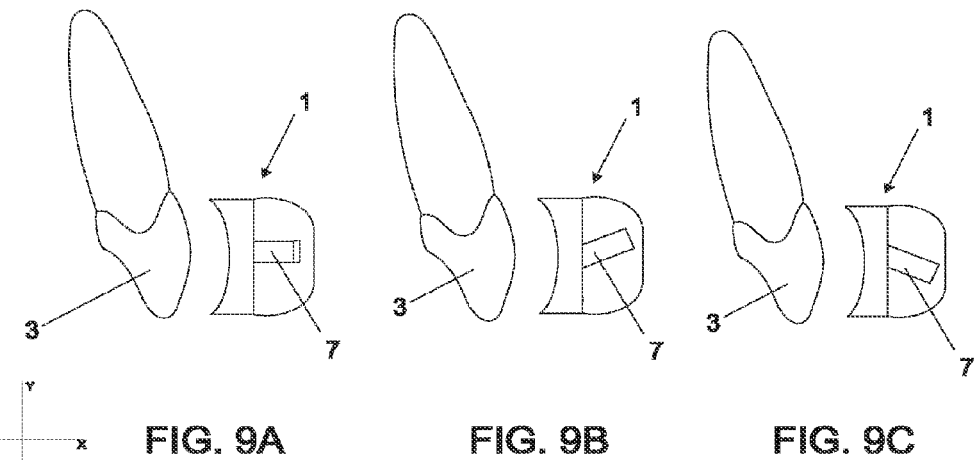
FIG. 9A: Illustration of a basic application wherein on a schematic side view the base and the lock to obtain neutral torque is shown.
FIG. 9B: Illustration of a basic application wherein on a schematic side view the base and the lock to obtain positive torque is shown.
FIG. 9C: Illustration of a basic application wherein on a schematic side view the base and the lock to obtain negative torque is shown.

The "BRACKET IMPROVEMENT WITH INTERCHANGEABLE LOCK" object of this request for Invention Patent "BRACKET IMPROVEMENT WITH INTERCHANGEABLE LOCK" encompass a bracket (1) formed by a base (2) of fixed construction arrangement to which the vestibular portion (3) of the tooth is adhered, in view of having angling (4) therefor, such base (2) with orthogonal projection (5) which can receive locks (6) overlapped with several angling and "groove" dimensions (7) shaped on its side wall (8) that, once overlapped to the base (2) creates an ideal passageway for conduction of wires (F) of different gauges, it being enough to change said locks (6) to fit the "grooves" (7) according to pressing treatment need, the same base (2) remaining throughout the treatment.

Therefore this invention is noted by the extreme flexibility achieved in orthodontic treatments in which around de same base (2), by varying said interchangeable locks (6) it is possible to fully change the treatment direction during its course.

Among the countless combination possibilities between bases (2) and locks (6), it should be remarked the fact that the base (2) is single and the lock (6) is interchangeable, perfectly adjustable to the base (2) so that, once overlapped it is shaped to the upper portion (9) of said base (2) through the cavity (10) existing in the lower portion of the lock (6), always compatible to be fitted into the base (2) through any already known means. On the other hand, after dully fitted the lock (6) is naturally aligned to the axis (E) of the base (2) in such a way that the "groove" (7) carved on the side walls (8) of said lock (6) in the desired configuration, together with the central gap (V) of the base (2) formed by the orthogonal projection (5), allows the passage of the traction wires (F), and also after the overlapping the now assemble takes on external round ergonomic shapes that do not interfere with the patient's mouth physiology.

Within the principle shown above, from the same base (2) it is possible to obtain countless groove combinations (7), such as locks (6) with side slots (11) for obtaining of neutral torque, wherein said slots (11), in the required size and compatible with the traction element, is parallel to the abscissa axis. To obtain positive torque with maintenance of the same base (2) the slot (11) carved on the sides (8) of the lock has an inclination within the first quadrant of the coordinate axis and to obtain negative torque said slot (11) has inclination located in the fourth quadrant of the coordinate axis.

Through maintenance of the same base (2) the bracket (1) can in addition to vary the torque direction, change the inclination as from a neutral, positive or negative angling in equal measure by simply changing the lock (6) that in the neutral position the slot (11) maintains parallelism on the side walls (8); in the positive inclination, on the other hand, the slots (11) are transversally shifted upstream toward the second quadrant of the coordinate axis and the negative inclination with the slots (11) transversally shifted downstream toward the first quadrant of the coordinate axis.

Another possibility concerns the flexibility possible in the width size, i.e., it is possible to have a bracket (1) adaptable to all possible sizes, such choice depending on the amount of control or positioning of the tooth as well.

The proposed bracket (1) also allows for the alteration of depth of the groove (7).

Figures 10A, 10B, 10C:
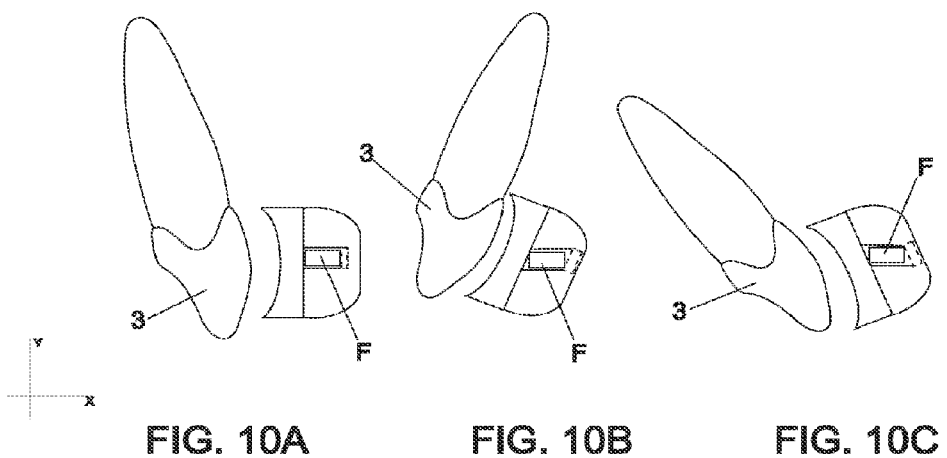
FIGS. 10A-C: Show a basic application wherein on a schematic side view the base and the lock with traction wire is shown, which can take the tooth from a positive extreme position (FIG. 10A), going through the neutral position (FIG. 10B) up to the negative extreme (FIG. 10C)
Figures 11A, 11B, 11C:
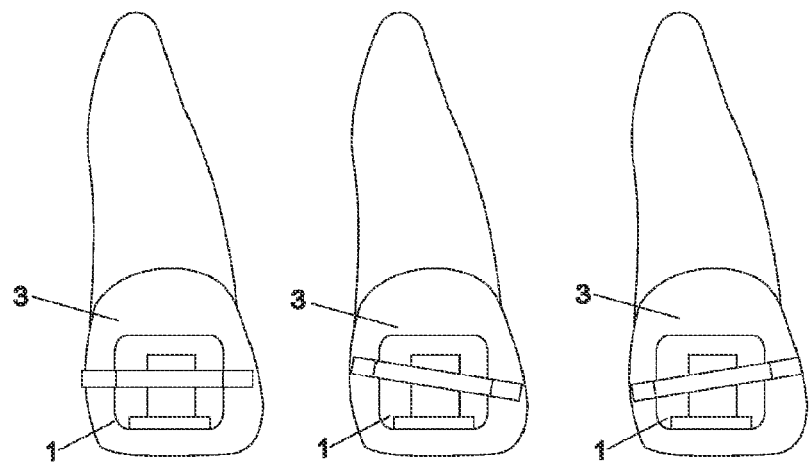
FIG. 11A: Illustration of a basic application wherein on a schematic side view the base and the lock for obtaining of neutral inclination is shown.
FIG. 11B: Illustration of a basic application wherein on a schematic side view the base and the lock for obtaining of positive inclination is shown.
FIG. 11C: Illustration of a basic application wherein on a schematic side view the base and the lock for obtaining of negative inclination is shown.

The bracket (1) when closed, i.e., with the lock (6) overlapped to the base (2) without the traction wire (F) obviously causes no alteration to the relative position of the teeth, since it is not subject to any kind of force. Therefore, with the distinctive locks (6) and torques it is possible with the same base (2) varying only the locks (6), to take a tooth from a positive extreme position, going through the neutral position up to a negative extreme position (FIGS. 10A-C).

Figures 12A, 12B, 12C:
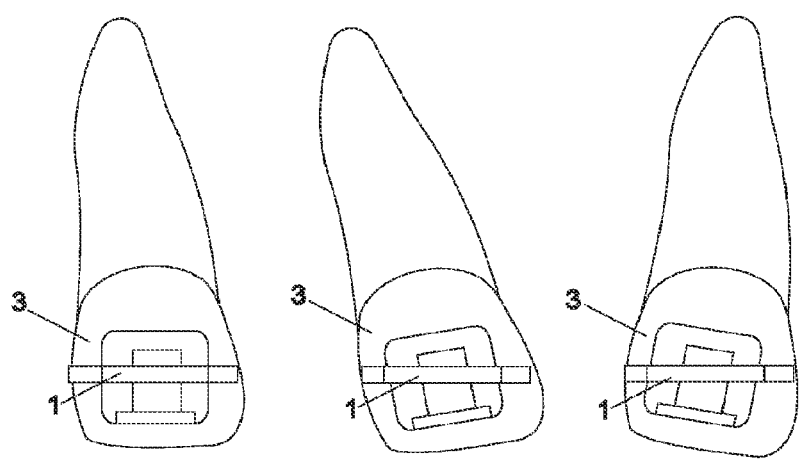
FIGS. 12A-C: Show a basic application wherein on a schematic side view the base and the lock with traction wire is sequentially shown, which takes the tooth from a positive extreme angling (FIG. 12A), going through the neutral position (FIG. 12B) up to the negative extreme (FIG. 12C)

With the same principle it is possible to obtain an extreme flexibility at the angling variation, going from a positive, neutral extreme up to the negative extreme (FIGS. 12A-C) in a simple and quick manner, it being enough to change the locks (6) in the wanted teeth.

Figure 13:
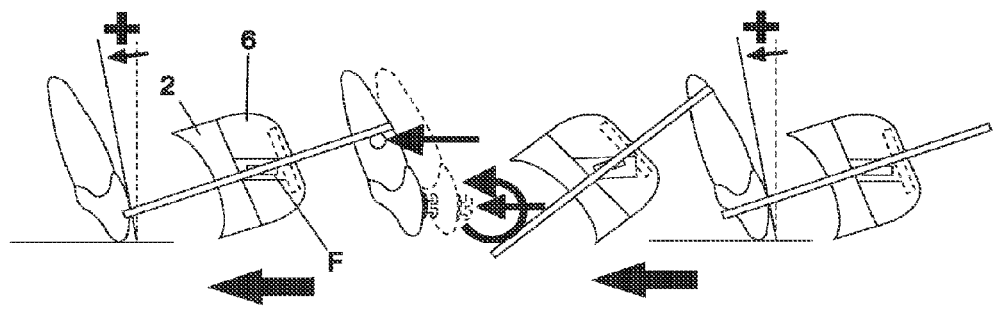
FIG. 13: Illustration of a basic application showing the sequence of the retraction movement of the new bracket with regard to a dental arch with extraction of the premolar.

Another possibility is the retracting movement, normal in cases of extraction (FIG. 13), so that with the proposed bracket (1) it is possible to change its torque only at the required moment, i.e., instead of opting for a bracket (1) with stronger torque to compensate the inclination/torque loss movement and adapt the finishing to the bracket (1) at the final stage or even change it, it is possible to use the lock (6) with stronger torque only during the retraction stage and after that return to the normal torque simply by changing the lock (6).

Figure 14:
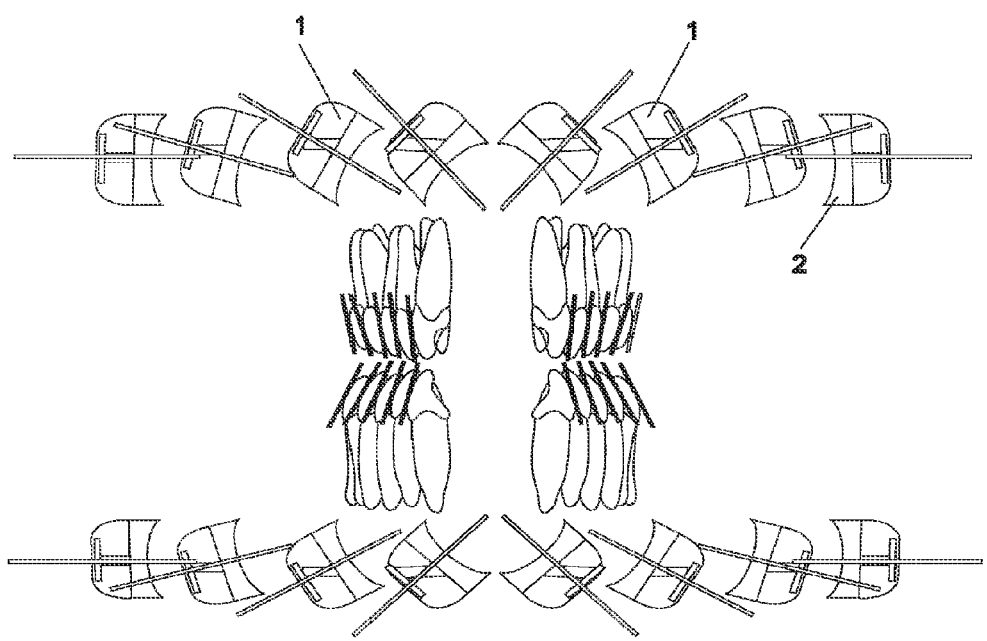
FIG. 14: Illustration of a basic application showing small changes in the teeth position both at the finishing and in the treatment mechanics with regard to a dental arch with extraction.
Figure 15:
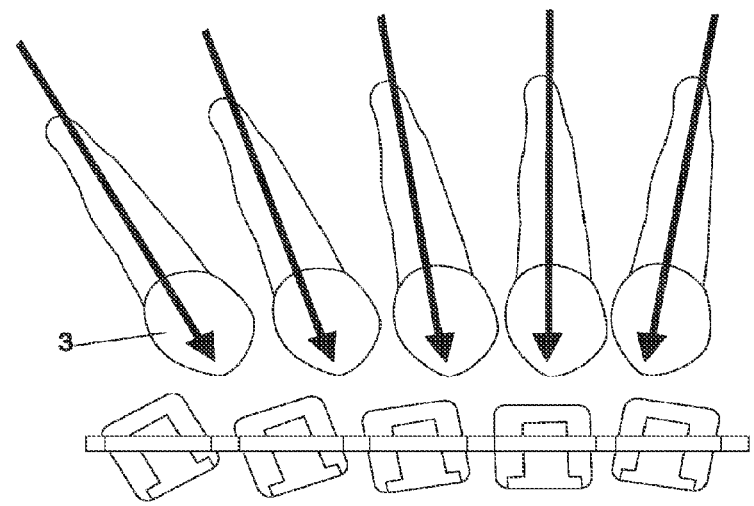
FIG. 15: Illustration of a basic application showing the flexibility possibility of the new bracket in relation to the new dental arch.
Figures 16A, 16B, 16C:
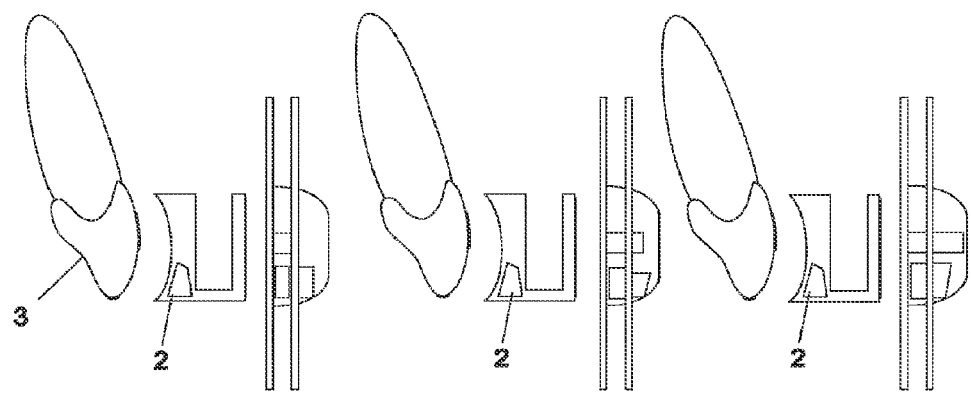
FIG. 16A: Illustration of the bracket on a schematic exploded side view showing a relatively narrow lock width.
FIG. 16B: Illustration of the bracket on a schematic exploded side view showing a relatively medium lock width.
FIG. 16C: Illustration of the bracket on a schematic exploded side view showing a relatively wide lock width.

Another flexibility of the bracket (1) claimed is the possibility of small changes in the teeth position both at the finishing and in the treatment mechanics. Quite subtle changes that, if made in the mouth, are exceedingly difficult due to the need to properly fold the traction wire and especially uncomfortable to the patient (FIG. 14).

What is claimed:
1. An orthodontic bracket system comprising:
a plurality of interchangeable locks (6);
a base (2) adapted to receive each of the plurality of interchangeable locks (6), the base having a rear surface (4) adapted to be adhered to a tooth, the base having a front surface opposite from the rear surface, an orthogonal projection (5) extending from the front surface of the base, the orthogonal projection having horizontal portion extending directly from the front surface and a vertical portion extending vertically from the horizontal portion spaced apart from the front surface of the base, whereby the front surface of the base, the horizontal portion of the orthogonal projection and the vertical portion of the orthogonal projection form a gap (V) for receiving and retaining a traction wire (F);
each of the interchangeable locks (6) including a body and a first vertically oriented wall (8) extending from the body and a second vertically oriented wall (8) spaced apart from the first vertically oriented wall, wherein a first transverse slot (11) is formed in the first vertically oriented wall and a second transverse slot (11) is formed in the second vertically oriented wall, wherein said first and second slots are open towards a rear of the lock, wherein said first and second slots have an incline angle, wherein said first slot has a first depth, wherein said second slot has a second depth, and wherein the first slot has a first relative height and the second slot has a second relative height; and wherein each of the interchangeable locks attaches to the base with the orthogonal projection (5) of the base (2) received in the space between the first and second vertically oriented walls (8) of the lock (6) and the rear of the lock in close engagement with the front surface of the base, wherein the orthogonal projection projects through the space between the walls and has a rounded exposed exterior surface and each of the plurality of locks has a complimentary rounded external shape that matches and aligns flush with the rounded exterior surface of the orthogonal projection to form a smooth rounded outer surface comprised of the base and lock; wherein the first and second slots and the gap form a traction wire retaining groove; and herein a direction of torque applied to the tooth is determined by the incline angle, the depths of the slots, and a difference between the relative heights of the slots, which may vary between the first and second slots of one particular lock and between each of the plurality of interchangeable locks.

\* \* \* \* \*